United States Patent
Duan et al.

(10) Patent No.: US 12,121,607 B2
(45) Date of Patent: Oct. 22, 2024

(54) FERMENTED BIRCH SAP AND METHOD FOR PRODUCING IT

(71) Applicant: ZHEJIANG YANGSHENGTANG INSTITUTE OF NATURAL MEDICATION CO., LTD., Hangzhou (CN)

(72) Inventors: Yingyi Duan, Hangzhou (CN); Xinyue Wang, Hangzhou (CN); Tao Hong, Hangzhou (CN)

(73) Assignee: Zhejiang Yangshengtang Institute of Natural Medication Co., Ltd., Hangzhou (CN)

(*) Notice: Subject to any disclaimer, the term of this patent is extended or adjusted under 35 U.S.C. 154(b) by 696 days.

(21) Appl. No.: 17/256,522

(22) PCT Filed: Jan. 21, 2020

(86) PCT No.: PCT/CN2020/073351
§ 371 (c)(1),
(2) Date: Dec. 28, 2020

(87) PCT Pub. No.: WO2021/017449
PCT Pub. Date: Feb. 4, 2021

(65) Prior Publication Data
US 2021/0177734 A1    Jun. 17, 2021

(30) Foreign Application Priority Data

Jul. 29, 2019    (CN) .......................... 201910689097.4

(51) Int. Cl.
| | | |
|---|---|---|
| *A61K 8/9789* | (2017.01) | |
| *A61K 8/9728* | (2017.01) | |
| *A61Q 19/00* | (2006.01) | |
| *A61Q 19/02* | (2006.01) | |
| *A61Q 19/08* | (2006.01) | |
| *C12P 1/02* | (2006.01) | |
| *C12P 7/22* | (2006.01) | |
| *C12P 19/04* | (2006.01) | |

(52) U.S. Cl.
CPC .......... *A61K 8/9789* (2017.08); *A61K 8/9728* (2017.08); *A61Q 19/00* (2013.01); *A61Q 19/02* (2013.01); *A61Q 19/08* (2013.01); *C12P 1/02* (2013.01); *C12P 7/22* (2013.01); *C12P 19/04* (2013.01); *A61K 2800/85* (2013.01)

(58) Field of Classification Search
None
See application file for complete search history.

(56) References Cited

U.S. PATENT DOCUMENTS

| | | |
|---|---|---|
| 10,799,445 B2 | 10/2020 | Jin et al. |
| 2019/0240134 A1 | 8/2019 | Zheng et al. |
| 2020/0046631 A1 | 2/2020 | Jin et al. |
| 2021/0093535 A1 | 4/2021 | Hu |

FOREIGN PATENT DOCUMENTS

| | | | |
|---|---|---|---|
| CN | 1556194 A | | 12/2004 |
| CN | 101368158 A | * | 2/2009 |
| CN | 103156052 A | * | 6/2013 |
| CN | 104956925 A | | 10/2015 |
| CN | 106107366 A | | 11/2016 |
| CN | 106420500 A | | 2/2017 |
| CN | 106434755 A | | 2/2017 |
| CN | 106978465 A | | 7/2017 |
| CN | 107019660 A | | 8/2017 |
| CN | 107049865 A | | 8/2017 |
| CN | 107586640 A | | 1/2018 |
| CN | 108265006 A | | 7/2018 |
| CN | 108420780 A | | 8/2018 |
| CN | 108635285 A | | 10/2018 |
| CN | 108676666 A | | 10/2018 |
| CN | 109044929 A | | 12/2018 |
| CN | 109055170 A | | 12/2018 |
| CN | 109077960 A | | 12/2018 |
| JP | H-10191783 A | | 7/1998 |
| JP | 3008292 B2 | | 2/2000 |
| KR | 20070055373 A | | 5/2007 |
| KR | 20100080972 A | | 7/2010 |
| WO | WO-2018115303 A1 | | 6/2018 |

OTHER PUBLICATIONS

Softa et al., Birch Sap (*Betula alba*) and Chaga Mushroom (*Inonotus obliquus*) Extracts Show Anti-Oxidant, Anti-Inflammatory and DNA Protection/Repair Activity In VitroJournal of Cosmetics, Dermatological Sciences and Applications, 9, 188-205, published Jun. 12, 2019 (Year: 2019).*
Database Accession No. 7636135 (Jun. 8, 2020). "Revitalizing Serum," Database GNPD, 6 total pages.
Shen, X-Y. et al. (2016). "Research progress on biological activity of inonotusobliquus," Guangzhou Chemical Industry 44:18-19 and 30 (with English Abstract).
Shen, Y. et al. (2017). "Research progress in nutrient composition function and utilization of birch sap," Farm Products Processing 7:49-52 (with English Abstract).
International Search Report mailed on Apr. 17, 2020, for PCT Application No. PCT/CN2020/073351, 3 pages (English translation).
Shen, X. et al. (2016). "Research Progress on Biological Activity of Inonotusobliquus," Guangzhou Chemical Industry, vol. 44, No. 10, pp. 18-19 and 30 (English Translation of Abstract Provided).

(Continued)

*Primary Examiner* — David J Blanchard
*Assistant Examiner* — Edwin Coleman Mitchell
(74) *Attorney, Agent, or Firm* — COOLEY LLP

(57) ABSTRACT

The present invention relates to a fermented birch sap and a method for producing it, wherein the fermented birch sap is obtained by fermentation using birch sap as a substrate and Inonotus obliquus as a strain; the method comprises the step of fermentation using birch sap as a substrate and Inonotus obliquus as a strain.

8 Claims, No Drawings

(56) References Cited

OTHER PUBLICATIONS

Sheng, Y. et al. (2017). "Research Progress in Nutrient Composition Function and Utilization of Birch Sap," Farm Products Processing, No. 7, pp. 49-52 (English Translation of Abstract Provided).

Chen, C., et al., "Submerged Fermentation Conditions for Synthesis of Extracellular Polysaccharide by *Inonotus obliquus*," Chinese Traditional and Herbal Drugs, 2007, vol. 38, No. 3, pp. 358-361 (English Translation of Abstract Provided).

Zhu, J., et al., "The Synthetics, Chemical Composition and Antioxidant Activity of Polyphenols in Submerged Cultures of *Inonotus obliquus*," Journal of Zhejiang University of Science and Technology, Jul. 2011, vol. 28, No. 4, pp. 616-620 (English Translation of Abstract Provided).

Office Action for Korean Application No. 1020217001641 mailed Jul. 30, 2024, 12 pages.

\* cited by examiner

FERMENTED BIRCH SAP AND METHOD FOR PRODUCING IT

RELATED APPLICATIONS

This application is a U.S. National Phase application, filed under 35 U.S.C. § 371 (c), of International Application No. PCT/CN2020/073351, filed Jan. 21, 2020, which claims priority to, and the benefit of, Chinese Patent Application No. 201910689097.4, filed Jul. 29, 2019, and the entire contents of both of which are herein incorporated by reference in their entirety.

TECHNICAL FIELD

The invention relates to a fermented birch sap and a method for producing it, wherein the fermented birch sap is obtained by fermentation using birch sap as a substrate and Inonotus obliquus as a strain; the method includes the step of fermentation using birch sap as a substrate and Inonotus obliquus as a strain.

BACKGROUND ART

Birch is a deciduous tree of the birch family, and there are about 100 species around the world at present, mainly distributed in the northern temperate zone and the cold temperate zone. Among them, there are about 29 species in China, mainly distributed in the northeast, northwest, and southwest. Birch trees mostly grow in remote mountainous areas with little human interference and no industrial pollution. Birch sap (also called birch juice) is fresh sap from the birch bark that is cut or from the trunk that is drilled. It is colorless or light yellow, has no precipitates or impurities, and has a light birch fragrance. Birch sap contains a large number of compounds such as sugars, amino acids, vitamins, biotin, cytokinins, trace mineral elements, aromatic oils, betulin, and saponin, and has good moisturizing, anti-inflammatory, anti-wrinkle, whitening and other skin care efficacy.

The use of birch sap in the existing fermentation process is limited to the field of beverages and wines. For example, CN107586640A discloses a fermentation process for birch sap wine, CN108676666A discloses a birch sap beer and brewing method thereof, in which birch sap is fermented by yeast to produce alcoholic beverages; CN109055170A discloses a Betula Alba sap vinegar and preparation method thereof, in which birch sap is fermented to obtain birch sap vinegar (total acid content of >3%) by alcoholic and acetic fermentation. Therefore, the existing processes for fermenting birch sap are aimed at increasing the content of ethanol or acetic acid in birch sap, which cannot make birch sap have other active ingredients, thereby limiting the use of fermented birch sap. CN109077960A discloses an anti-aging and whitening composition comprising Betula Alba sap, although fermented birch sap is used as a cosmetic raw material, the fermentation strain, functional ingredients and efficacy of the raw material are unknown, and the fermentation cycle is as long as 30 days and the production yield is very low.

Inonotus obliquus, commonly known as Chaga mushroom, belongs to Basidiomycotina, Hymenomycetes, Aphyllophorales, Polyproranceae, Poria hypobrunnea Petch. Inonotus obliquus contains more than ten trace elements such as carbon, potassium, nitrogen, calcium, and aluminum etc, as well as active substances such as proteins, polysaccharides, flavones, polyphenols, sterols, alkaloids, peptides, and organic acids etc. These active substances produced by Inonotus obliquus have anti-oxidation, anti-inflammatory, immunoregulation and other biological activities, and have good application prospects.

Submerged fermentation technology can shorten the growth cycle of Inonotus obliquus, obtain a large amount of mycelia in a short time, and make Inonotus obliquus accumulate a large amount of intracellular and extracellular products. Although the fermented filtrate of Inonotus obliquus contains polyphenols, polysaccharides and other active ingredients (Zhu Jinwei et al., 2011, Journal of Zhejiang University of Science and Technology, Vol. 28, No. 4, pages 616-620; Chen Caifa et al., 2007, Chinese Herbal Medicine, No. 3, pages 358-361), the existing submerged fermentation process for Inonotus obliquus focuses on obtaining mycelium biomass and intracellular products (triterpenes, polysaccharides, etc.), see, for example, CN160978465A, which discloses a fermentation method for increasing the yield of total triterpenes.

In addition, the fermented filtrate of Inonotus obliquus is often treated with organic solvents or by concentration in the prior art. For example, CN104956925A discloses a method of producing fermentation broth and fermentation powder by continuous submerged fermentation of Inonotus obliquus, in which the fermented filtrate is subjected to concentration treatment, thereby resulting in a high process cost; CN106434755A discloses a submerged fermentation broth of Inonotus obliquus and use thereof, wherein the fermentation broth is eluted with ethanol, the use of organic solvents is likely to cause environmental pollution and increase energy consumption.

Based on the status of the prior art, the present invention attempts to expand the use of fermented birch sap and improve the use situation of the fermented filtrate of Inonotus obliquus.

Contents of the Invention

The present inventors have found that, a fermented birch sap filtrate with improved performances can be obtained by fermentation using Inonotus obliquus as strain and birch sap as sole or main substrate, and the fermented birch sap filtrate has the active ingredients of birch sap itself and is also rich in polysaccharides, polyphenols and other active ingredients, and thereby can be advantageously used as an active raw material for skin topical compositions.

Therefore, in one aspect, the present invention relates to a method for producing a fermented birch sap filtrate, comprising the step of fermentation using birch sap as a substrate and Inonotus obliquus as a strain.

In a preferred embodiment, the method further comprises in situ thermal extraction of the fermentation broth obtained in the fermentation step in a fermentation tank to release the intracellular polysaccharides and polyphenols of Inonotus obliquus into the fermentation broth.

In one embodiment, the in situ thermal extraction comprises heating the fermentation broth to about 60-95° C., preferably about 65-90° C., more preferably about 70-85° C., and holding for about 30-150 mins, preferably about 40-100 mins, more preferably about 50-80 mins; and then cooling to about 18-30° C., preferably about 20-28° C.

Generally, the method for producing a fermented birch sap specifically includes the following steps:
(1) preparing a seed broth,
(2) preparing a birch sap fermentation medium,
(3) inoculating and fermenting to obtain a fermentation broth, Optionally, (4) in situ thermal extracting the fermentation broth, and (5) centrifuging the fermentation broth to remove mycelia, and filtrating supernatant to obtain a fermented birch sap filtrate (i.e. the fermented birch sap).

The preparation of seed broth in the step (1) is known in the art. For example, the Inonotus obliquus scraped off the solid medium plate can be inoculated into a shake flask containing a certain amount (e.g. 50 mL) of seed culture medium, and incubated at a temperature of 25-30° C. and a shaker speed of 150-180 rpm for 4-6 days to obtain a primary seed broth; the primary seed broth is transferred into a shake flask containing a certain amount (e.g. 400 mL) of seed culture medium at inoculation amount of 5-10%, and incubated at a constant temperature of 25-30° C. and a shaker speed of 150-180 rpm for 2-3 days to obtain a secondary seed broth.

In the step (1), the preferred solid culture medium is PDA medium, which comprises 1000 mL of deionized water, 0.6% potato extract powder, 2% glucose, and 1.5% agar. The preferred seed culture medium is oat germ bran medium, which comprises 1000 mL of deionized water, 3% glucose, 1% oat germ bran powder, 1% yeast powder, 0.1% potassium dihydrogen phosphate, and 0.05% anhydrous magnesium sulfate, natural pH.

In the step (2), the birch sap fermentation medium is prepared by using birch sap as the sole substrate, and optionally adding a carbon source, a nitrogen source, an inorganic salt and/or a pH adjuster to the substrate.

The birch sap is obtained from Betula Betulaceae, including Betalaalba, Betula pubescens, Betula Pendula, and Betula platyphylla. The birch sap is a colorless, transparent and nutritious birch sap without precipitates or impurities obtained by artificially drilling and collecting from the base of the trunk of a birch tree from the time when the snow begins to melt to the time when the trees foliate. The birch sap is commercially available and used as it is (in this case, it is also called as un-concentrated birch sap, or birch sap stock solution), for example, it can be purchased from Daxinganling Chaoyue Wild Berry Development Co., Ltd.

The birch sap may be a birch sap stock solution or a concentrated birch sap, wherein the concentrated birch sap has a concentration degree of 1.2-6 times, preferably 1.5-4 times.

The concentrated birch sap is obtained by concentrating the above-mentioned commercially available birch sap. Concentration methods are known in the art, such as heating concentration, low-temperature and vacuum concentration, and membrane concentration etc. In the present invention, the concentration is preferably performed by a low-temperature freeze concentration or membrane concentration process etc. For example, a commercially available birch sap stock solution product is introduced into a low-temperature drying device, cooled to −40 to −70° C., and vacuumed to 0.1-30 Pa for low-temperature and vacuum concentration to obtain a concentrated birch sap having different concentration degrees.

In one embodiment, the birch sap fermentation medium can use birch sap as the sole substrate without adding any additional ingredients thereto, including not adding any additional water, but not excluding the moisture inherently comprised in each of the components.

In one embodiment, a carbon source, a nitrogen source, an inorganic salt, and/or a pH adjuster can be optionally added to the birch sap as needed.

The carbon source is known in the art and include, but are not limited to, glucose, glycerol, molasses, lactose, mannose, maltose, corn starch, sucrose, and fructose etc. In the present invention, glucose is preferred. The content of the carbon source in the birch sap fermentation medium is typically about 0-3.5%, preferably about 0.5-3%, based on the total weight of the birch sap fermentation medium.

The nitrogen source is known in the art and include, but are not limited to, whey protein, plant protein, cereal flour, hydrolyzed plant polypeptide, yeast powder, and tryptone. In the present invention, the preferred whey protein is isolated whey protein powder; the preferred plant protein is pea powder and hydrolyzed pea protein; and the preferred cereal flour is rye flour, hydrolyzed oat flour, and hydrolyzed brown rice flour. The content of the nitrogen source in the birch sap fermentation medium is typically about 0-3%, preferably about 0.3-2.5%, based on the total weight of the birch sap fermentation medium.

The inorganic salt is known in the art and include, but are not limited to, potassium dihydrogen phosphate, magnesium sulfate, sodium dihydrogen sulfate, and calcium chloride. In the present invention, potassium dihydrogen phosphate and anhydrous magnesium sulfate are preferred. The content of the inorganic salt in the birch sap fermentation medium is typically about 0-0.3%, preferably about 0.05-0.1%, based on the total weight of the birch sap fermentation medium.

The pH adjuster is known in the art and include, but are not limited to, citric acid, sodium citrate, lactic acid, sodium lactate, and sodium hydroxide. In the present invention, citric acid and sodium citrate are preferred. Optionally, the pH of the birch sap fermentation medium is adjusted to about 5.0-6.5 using a pH adjuster depending on the initial pH of the birch sap raw material.

In the case where a carbon source, a nitrogen source, an inorganic salt, and/or a pH adjuster are comprised in the fermentation medium, a birch sap fermentation medium can be prepared by adding these materials to birch sap. In the case where a carbon source, a nitrogen source, an inorganic salt, and/or a pH adjuster are comprised in the fermentation medium, the content of birch sap in the fermentation medium is about 90% or more, preferably about 93% or more, based on the total weight of the birch sap fermentation medium.

The inoculating and fermenting of the step (3) is known in the art. For example, the birch sap fermentation medium of step (2) is added at a loading volume of about 60-70% (v/v) to a 100-12,000 L fermentation tank, and sterilized at 121° C. for 20-40 mins; based on the volume of fermentation medium for the fermentation, the secondary seed broth is inoculated at an inoculation amount of about 5-10% into the fermentation tank under aseptic conditions, and continuously fermented at a temperature of about 25-30° C., a stirring speed of 180-250 rmp, and an aeration of 1.2-2.0 vvm for 7-9 days, then the fermentation operation is terminated, i.e. the fermentation process is completed, and a fermentation broth is obtained.

The in-situ thermal extracting of the step (4) involves in-situ thermal extracting the fermentation broth obtained in the step (3) in the fermentation tank to release the intracellular polysaccharides and polyphenols of Inonotus obliquus into the fermentation broth. In one embodiment, step (4) comprises heating the fermentation broth obtained in the step (3) to about 60-95° C., preferably about 65-90° C., more preferably about 70-85° C., and holding for about 30-150 mins, preferably about 40-100 mins, more preferably about 50-80 mins; and then cooling to about 18-30° C., preferably about 20-28° C.

The centrifuging and filtrating of the step (5) is known in the art, and is typically performed at 6000-10,000 rpm for 15-30 mins. In the centrifugation step, a supernatant is obtained by centrifuging the fermentation broth to remove mycelia, and the supernatant is filtered to obtain the fermented birch sap filtrate product.

The method of the present invention may further comprises subjecting the obtained filtrate product to ultra-high temperature instantaneous sterilization at a temperature of (115±5)° C. for 10-30 seconds. The sterilized fermented birch sap filtrate product is then transferred to a storage tank for storage.

The fermented birch sap filtrate product (also referred to as fermented birch sap) obtained by the above method is light in color, and transparent. It contains not only the nutritional ingredients of the birch sap substrate itself (including B vitamins, trace elements, amino acids, fatty acids etc.), but also total phenols of about 100 mg/L or more, preferably about 130 mg/L or more, more preferably about 150 mg/L or more, and polysaccharides of about 1.3 g/L or more, preferably 1.8 g/L or more, more preferably about 3.0 g/L or more. The method for determining total phenols is folin-ciocalteu colorimetry, and the method for determining extracellular polysaccharides is anthrone-sulfuric acid colorimetry. The total phenols as determined mainly include gallic acid, ferulic acid, naringin, quercetin, and kaempferol.

The method of the present invention has the following advantages and effects as compared to those in the prior art:
(1) by using Inonotus obliquus as the starting strain and birch sap as the main substrate for fermentation, the resulting fermented birch sap filtrate has increased total phenols, polysaccharides and other active ingredients than the raw material birch sap, so that the fermented birch sap product has excellent tyrosinase activity inhibition and antioxidation activity, and therefore has better skin topical efficacy, such as skin care efficacy, which expands the use scope of fermented birch sap, and makes it no longer to be limited to the use only for beverages and wines;
(2) no organic solvents are used in the treatment process for the fermented birch sap filtrate, which is green and environmentally friendly, and has strong operability;
(3) the obtained fermented birch sap filtrate can be directly used without concentration process, thereby the utilization rate of raw materials is improved and production costs are reduced;
(4) the formulation of the birch sap fermentation medium is optimized, glucose and plant protein are used as carbon and nitrogen sources for the fermentation of Inonotus obliquus, the raw materials are easily available and the cost is low; the fermented filtrate obtained with the optimized fermentation medium is light in color, and transparent, and has better features than the fermentation broths of Inonotus obliquus as reported in the prior art.

In yet another aspect, the present invention further relates to the use of fermented birch sap product in a skin topical composition, wherein the fermented birch sap is obtained by fermentation using birch sap as a substrate and Inonotus obliquus as a strain. In a preferred embodiment, the fermented birch sap filtrate product comprises total phenols of 100 mg/L or more, preferably 130 mg/L or more, more preferably 150 mg/L or more, and polysaccharides of 1.3 g/L or more, preferably 1.8 g/L, more preferably 3.0 g/L.

In yet another aspect, the present invention further relates to a skin topical composition, comprising (A) fermented birch sap, wherein the fermented birch sap is obtained by fermentation using birch sap as a substrate and Inonotus obliquus as a strain.

In a preferred embodiment, the fermented birch sap filtrate product comprises total phenols of 100 mg/L or more, preferably 130 mg/L or more, more preferably 150 mg/L or more, and polysaccharides of 1.3 g/L or more, preferably 1.8 g/L, more preferably 3.0 g/L.

The content of the fermented birch sap in the skin topical composition can be varied within a wide range, for example, can be about greater than 0 to less than 100%, preferably about 80-95%, based on the total weight of the skin topical composition.

The skin topical composition includes a pharmaceutical composition or a cosmetic composition, especially a skin care cosmetic composition, a whitening cosmetic composition, and an anti-aging cosmetic composition.

In addition to (A) the fermented birch sap, the skin topical composition may optionally further comprise (B) an ingredient commonly used in skin topical compositions, including, but not limited to a vehicle, an active ingredient, and an excipient etc. Component (B) is known in the art, and those skilled in the art can select its type and amount as required. For example, the content of component (B) is about 2-82%, based on the total weight of the skin topical composition.

The vehicle includes, for example, a diluent, a dispersant, or a carrier. Examples include, but are not limited to, ethanol, dipropylene glycol, and butanediol. The content of the vehicle in the skin topical composition is known in the art, for example, it is typically 0.5-20%, based on the total weight of component (B).

The active ingredient includes, for example, an emollient, a humectant, a whitening active ingredient, and an anti-aging active ingredient.

Examples of the emollient include, but are not limited to, one or more of olive oil, macadamia nut oil, sweet almond oil, grape seed oil, avocado oil, corn oil, sesame oil, soybean oil, peanut oil, meadowfoam seed oil, safflower seed oil, rosa canina, fruit oil, argania spinosa kernel oil, *simmondsia chinensis* seed oil, sunflower seed oil, mauritia flexuosa fruit oil, squalane, ethylhexyl palmitate, isopropyl myristate, hydrogenated polyisobutylene, isocetane, isododecane, diethylhexyl carbonate, dioctyl carbonate, isopropyl lauroyl sarcosinate, isononyl isononanoate, hydrogenated polydecene, triethylhexanoin, cetyl ethylhexanoate, bis-ethoxydiglycol cyclohexane 1,4-dicarboxylate, caprylic/capric triglyceride, oleyl erucate, octyldodecanol myristate, octyldodecanol, polydimethylsiloxane, octyl polymethylsiloxane, cetyl dimethicone, and decamethylcyclopentasiloxane. Examples of solid emollient include, but are not limited to, one or more of cetyl alcohol, stearyl alcohol, cetearyl alcohol, behenyl alcohol, squalyl alcohol, lauric acid, myristic acid, palmitic acid, stearic acid, beeswax, candelilla wax, carnauba wax, lanolin, ozokerite, jojoba seed wax, paraffin wax, microcrystalline wax, hydrogenated rice bran wax, hydrogenated cocoglycerides, glyceryl behenate/eicosadioate, myristyl myristate, bis-diglyceryl polyacyladipate-2, butyrospermum parkii (shea butter), and astrocaryum murumuru seed butter. The content of the emollient in the skin topical composition is known in the art, for example, it is typically 1-50%, based on the total weight of the component (B).

Examples of the humectant include, but are not limited to, one or more of glycerol, diglycerol, butanediol, propylene glycol, 1,3-propanediol, dipropylene glycol, 1,3-propanediol, polyethylene glycol-8, polyethylene glycol-32, methyl gluceth-10, methyl gluceth-20, PEG/PPG-17/6 copolymer, glycereth-7, glycereth-26, glyceryl glucoside, PPG-10 methyl glucose ether, PPG-20 methyl glucose ether, PEG/PPG/polybutylene glycol-8/5/3 glycerol, sucrose, trehalose, rhamnose, mannose, raffinose, betaine, erythritol, xylitol, urea, glycereth-5 lactate, sodium hyaluronate, hydrolyzed sodium hyaluronate, acetylated sodium hyaluronate, sodium polyglutamate, hydrolyzed sclerotium gum, pululan, tremellarn, and tamarindus indica seed polysaccharide. The content of the humectant in the skin topical composition is known in the art, for example, it is typically 1-30%, based on the total weight of the component (B).

The whitening active ingredient includes, but is not limited to, one or more of kojic acid, ascorbyl glucoside, arbutin, tranexamic acid, nicotinamide, phytosterol, phytosteryl/behenyl/octyldodecyl lauroyl glutamate, phenethyl resorcinol, Curcuma Longa, Betula Platyphylla Japonica bark extract, ceramide 2, ceramide 3, acetyl-phytosphingosine, resveratrol, Pterocarpus Marsupium bark extract, Coleus Forskohlii root extract, Piper Nigrum (Pepper) seed extract, ubiquinone, cholesterol, cholesteryl stearate, ascorbic acid, ascorbic dipalmitate, tocopherol (vitamin E), tocopheryl acetate, bisabolene, ascorbyl tetraisopalmitate, pyridoxine dicaprylate, pyridoxine dipalmitate, retinyl palmitate, phytosteryl/octyldodecyl lauroyl glutamate, bisbehenyl/isostearyl/phytosteryl dimer dilinoleyl dimer dilinoleate, phytosteryl macadamiate, various peptides, and various plant extracts etc. The content of the whitening active ingredient in the skin topical composition is known in the art, for example, it is typically 0.01-30%, based on the total weight of the component (B).

Examples of the anti-aging active ingredient include, but are not limited to, one or more of tocopherol (vitamin E), retinol, retinyl palmitate, hydrolyzed collagen, hydrolyzed elastin, allantoin, yeast extract, oryzanol, tetrahydrocurcumin, ellagic acid, ubiquinone, whey protein, peptides, acetyl hexapeptide-8, palmitoyl pentapeptide-4, salicyloyl phytosphingosine, concentrated birch sap, silymarin, sericin, sodium tocopheryl phosphate, ribonucleic acid (RNA), dipeptide diaminobutyroyl ben zylalni de diacetate, palmitoyl tripeptide-5, oligopeptide-1, hexapeptide-9, palmitoyl oligopeptide, palmitoyl tetrapeptide-7, Vitis vinifera seed extract, Pterocarpus marsupium bark extract, Camellia sinensis polyphenols, wine extract, apple seed extract, Fagus sylvatica bud extract, Adansonia digitata extract, Artemia extract, Iris florentina root extract, hesperidin, ginsenoside, Salvia miltiorrhiza extract, nicotinamide, ursolic acid, sodium hyaluronate, acetylated sodium hyaluronate, hydrolyzed sodium hyaluronate, lycopene, Coffea arabica extract, dipeptide-2, lactic acid, superoxide dismutase (SOD), Oenothera biennis oil, ceramide, dipalmitoyl hydroxyproline, hydroxystearic acid, salicylic acid, ergothioneine, lysolecithin, carnosine, decarnosine HCL, lipoic acid, adenosine, glycogen, resveratrol, ferulic acid, Bifida ferment lysate, and Lactococcus ferment lysate etc. The content of the anti-aging active ingredient in the skin topical composition is known in the art, for example, it is typically 0.01 to 10%, based on the total weight of component (B).

The excipient includes, for example, an emulsifier, a thickener, a preservative, a perfume etc.

Examples of the emulsifier include, but are not limited to, one or more of cetearyl olivate, sorbitan olivate, polysorbate-60, polysorbate-80, methyl glucose sesquistearate, PEG-20 methyl glucose sesquistearate, PEG-40 hydrogenated castor oil, PPG-26-buteth-26, PEG-4 polyglyceryl-2 stearate, PEG-60 hydrogenated castor oil, steareth-2, steareth-21, PPG-13-decyltetradeceth-24, cetearyl glucoside, PEG-100 stearate, glyceryl stearate, glyceryl stearate SE, coco glucoside, ceteareth-25, PEG-40 stearate, polyglyceryl-3 methyl glucose distearate, glyceryl stearate citrate, polyglyceryl-10 stearate, polyglyceryl-10 myristate, polyglyceryl-10 dioleate, polyglyceryl-10 laurate, polyglyceryl-10 isostearate, polyglyceryl-10 oleate, polyglyceryl-10 diisostearate, polyglyceryl-6 laurate, polyglyceryl-6 myristate, sucrose stearate, and sucrose polystearate etc. The content of the emulsifier in the skin topical composition is known in the art, for example, it is typically 0.5-10%, based on the total weight of the component (B).

Examples of the thickener include, but are not limited to, one or more of high molecular polymers such as carbomers, acrylates and derivatives thereof, xanthan gum, gum arabic, polyethylene glycol-14M, polyethylene glycol-90M, succinyl polysaccharides, hydroxyethyl cellulose, hydroxypropyl cellulose, and hydroxypropyl methyl cellulose etc. The content of the thickener in the skin topical composition is known in the art, for example, it is typically 0.1-10%, based on the total weight of the component (B).

Examples of the preservative include, but are not limited to, one or more of methyl hydroxybenzoate, propyl hydroxybenzoate, phenoxyethanol, benzyl alcohol, phenylethanol, bis(hydroxymethyl)imidazolidinyl urea, potassium sorbate, sodium benzoate, chlorophenesin, sodium dehydroacetate, caprylhydroxamic acid, 1,2-hexanediol, 1,2-pentanediol, p-hydroxyacetophenone, caprylyl glycol, glyceryl caprylate, glyceryl undecylenate, sorbitan caprylate, ethylhexyl glycerol, and peony root extract etc. The content of the preservative in the skin topical composition is known in the art, for example, it is typically 0.01-2%, based on the total weight of the component (B).

The fermented birch sap filtrate may be mixed with other pharmaceutical or cosmetic ingredients by any of known methods in the industry for skin topical composition (pharmaceutical composition or cosmetic composition) to obtain a pharmaceutical composition or cosmetic composition. The other pharmaceutical or cosmetic ingredients mentioned above are the (B) an ingredient commonly used in skin topical compositions.

The skin topical composition can be prepared into various product forms, such as solution, suspension, ointment, cream, lotion, gel, powder or spray etc., as needed.

EXAMPLES

The present invention is further described in detail below with reference to examples. However, it should be understood that these examples and comparative examples are only used to specifically illustrate the present invention, and should not be understood to limit the scope of the appended claims of the present invention in any manner.

In the following examples, the Inonotus obliquus strain used in Examples 1-5 were deposited at the China Forestry Microbial Species Conservation and Management Center (strain code cfcc 6584). The yeast (*Saccharomyces cerevisiae*) strain used in Comparative Examples 5-8 was from Angel Yeast Co., Ltd. (strain number ANGEL 1021).

Example 1: Preparation of a Fermented Birch Sap Filtrate (1) Preparation of seed broth Inonotus obliquus was scraped off solid PDA medium plate, inoculated into a shake flask containing 50 mL of seed medium, and incubated at a temperature of 28° C. and a shaker speed of 150 rpm for 4 days to obtain a primary seed broth; the primary seed broth was transferred into a shake flask containing 400 mL of seed culture medium at an inoculation amount of 10%, and incubated at a constant temperature of 28° C. and 150 rpm for 2 days to obtain a secondary seed broth; wherein the seed culture medium comprised 1000 mL of deionized water, 3% glucose, 1% oat germ bran powder, 1% yeast powder, 0.1% potassium dihydrogen phosphate, and 0.05% anhydrous magnesium sulfate, natural pH.

(2) Preparation of birch sap fermentation medium

To the birch sap stock solution (brix 0.875) collected at Daxing'an Mountain, Northeast as a substrate were added 2% glucose as a carbon source, 0.3% whey protein (WPI90, commercially available from Fonterra Group of New Zealand) as a nitrogen source, 0.1% potassium dihydrogen phosphate, and 0.05% anhydrous magnesium sulfate, and the pH of the birch sap fermentation medium was adjusted to 5.5 with a 1M citric acid aqueous solution.

(3) Inoculation and fermentation

The birch sap fermentation medium prepared in the above step (2) was added at a loading volume of 60% (v/v) to a 300 L fermentation tank, and sterilized at 121° C. for 30 mins; based on the volume of fermentation medium for fermentation, the secondary seed broth was inoculated at an inoculation amount of 5% into the fermentation tank under aseptic conditions, and continuously fermented at 30° C., 200 rmp, and an aeration of 1.8 vvm for 7 days, then the fermentation operation was terminated to obtain a fermentation broth.

(4) Preparation of a fermented birch sap filtrate

The fermentation broth obtained in the above step (3) was in-situ heated in the tank to 90° C., held for 60 mins, cooled to 28° C., and then centrifuged at 6000 rpm for 30 mins to remove mycelia; the supernatant obtained by centrifugation was filtered by diatomaceous plate-and-frame filter to obtain the Inonotus obliquus-fermented birch sap filtrate; further, the obtained filtrate was sterilized by an ultra-high temperature instantaneous sterilization at a temperature of 120° C. for 30 seconds, and the sterilized fermented birch sap filtrate was transferred to a storage tank for storage.

(5) The fermented birch sap filtrate was determined for the content of total phenols and polysaccharides. The results were shown in Table 1.

Example 2: Preparation of Fermented Birch Sap Filtrate (1) Preparation of seed broth The preparation procedure of the seed broth was as described in Example 1;

(2) Preparation of birch sap fermentation medium

To the birch sap stock solution (brix 1.3) collected in Finland as a substrate were added 1.5% glucose as a carbon source, 1% pea flour (commercially available from Cargill Grain and Oil (Nantong) Co., Ltd.) as a nitrogen source, 0.1% potassium dihydrogen phosphate, and 0.05% anhydrous magnesium sulfate, and the pH of the birch sap fermentation medium was adjusted to 5.8 with a 1M sodium citrate aqueous solution.

(3) Inoculation and fermentation

The birch sap fermentation medium prepared in the above step (2) was added at a loading volume of 65 (v/v) to a 100 L fermentation tank, and sterilized at 121° C. for 30 mins; based on the volume of fermentation medium for fermentation, the secondary seed broth was inoculated at an inoculation amount of 7% into the fermentation tank under aseptic conditions, and continuously fermented at 30° C., 200 rmp, and an aeration of 1.6 vvm for 7 days, then the fermentation operation was terminated to obtain a fermentation broth.

(4) Preparation of fermented birch sap filtrate

The fermentation broth obtained in the above step (3) was in-situ heated in the tank to 80° C., held for 90 mins, cooled to 25° C., and then subjected to centrifugation, filtration, and heat sterilization as described in Example 1.

(5) The fermented birch sap filtrate was determined for the content of total phenols and polysaccharides. The results were shown in Table 1.

Example 3: Preparation of Fermented Birch Sap Filtrate (1) Preparation of seed broth The preparation procedure of the seed broth was as described in Example 1.

(2) Preparation of birch sap fermentation medium

To the birch sap concentrate (concentration degree of 3 times, brix 3.58, which was made from the birch sap stock solution from Xiaoxing'an Mountain, Northeast) as a substrate were added 0.5% glucose as a carbon source, 3% hydrolyzed oat protein (commercially available from Xiamen Biograin Biological Technology) as a nitrogen source, 0.1% potassium dihydrogen phosphate, and 0.05% anhydrous magnesium sulfate, and the pH of the birch sap fermentation medium was adjusted to 6.0 with a 1M sodium citrate aqueous solution.

(3) Inoculation and fermentation

The birch sap fermentation medium prepared in the above step (2) was added at a loading volume of 65 (v/v) to a 500 L fermentation tank, and sterilized at 121° C. for 30 mins; based on the volume of fermentation medium for fermentation, the secondary seed broth was inoculated at an inoculation amount of 10% into the fermentation tank under aseptic conditions, and continuously fermented at 30° C., 220 rmp, and an aeration of 1.8 vvm for 7 days, then the fermentation operation was terminated to obtain a fermentation broth.

(4) Preparation of fermented birch sap filtrate

The fermentation broth obtained in the above step (3) was in-situ heated in the tank to 65° C., held for 120 mins, cooled to 28° C., and then subjected to the centrifugation, filtration, and heat sterilization as described in Example 1.

(5) The fermented birch sap filtrate was determined for the content of total phenols and polysaccharides. The results were shown in Table 1.

Example 4: Preparation of Fermented Birch Sap Filtrate (1) Preparation of seed broth The preparation procedure of the seed broth was as described in Example 1.

(2) Preparation of birch sap fermentation medium

To the birch sap concentrate (concentration degree of 1.5 times, brix 1.8, which is made from the birch sap stock solution from Xiaoxing'an Mountain, Northeast) as a substrate were added 1.5% glucose as a carbon source, 3% hydrolyzed pea protein (commercially available from ROQUETTE (China) Co., Ltd.) as a nitrogen source, 0.1% potassium dihydrogen phosphate, and 0.05% anhydrous magnesium sulfate, and the pH of the birch sap fermentation medium was adjusted to 6.0 with a 1M sodium citrate aqueous solution.

(3) Inoculation and fermentation

The procedures of the inoculation and fermentation were as described in Example 1.

(4) Preparation of fermented birch sap filtrate

The fermentation broth obtained in the above step (3) was subjected directly to the centrifugation, filtration, and heat sterilization as described in Example 1, without undergoing thermal extraction in the fermentation tank.

(5) The fermented birch sap filtrate was determined for the content of total phenols and polysaccharides. The results were shown in Table 1.

Example 5: Preparation of Fermented Birch Sap Filtrate (1) Preparation of seed broth The preparation procedure of the seed broth was as described in Example 1.

(2) Preparation of birch sap fermentation medium

The birch sap concentrate (concentration degree of 3 times, brix 3.58, which is made from the birch sap stock solution from Xiaoxing'an Mountain, Northeast) in Example 3 was used as raw material, without adding a carbon source, a nitrogen source, an inorganic salt, and a pH adjuster.

(3) Inoculation and fermentation

The procedures of the inoculation and fermentation were as described in Example 3.

(4) Preparation of fermented birch sap filtrate

The preparation procedures of the fermented birch sap filtrate were as described in Example 3.

(5) The fermented birch sap filtrate was determined for the content of total phenols and polysaccharides. The results were shown in Table 1.

Comparative Example 1: Preparation of Unfermented Birch Sap Filtrate (1) Preparation of birch sap medium The preparation and sterilization procedures of birch sap medium were as described in Example 1.

(2) Preparation of unfermented birch sap filtrate

The birch sap medium was not subjected to inoculation and fermentation, and the preparation procedures of unfermented birch sap filtrate were as described in the step (4) of Example 1.

(3) The unfermented birch sap filtrate was determined for the content of total phenols and polysaccharides. The results were shown in Table 1.

Comparative Example 2: Preparation of Unfermented Birch Sap Filtrate (1) Preparation of birch sap medium The preparation and sterilization procedures of birch sap medium were as described in Example 2.

(2) Preparation of unfermented birch sap filtrate

The birch sap medium was not subjected to inoculation and fermentation, and the preparation procedures of unfermented birch sap filtrate were as described in the step (4) of Example 2.

(3) The unfermented birch sap filtrate was determined for the content of total phenols and polysaccharides. The results were shown in Table 1.

Comparative Example 3: Preparation of Unfermented Birch Sap Filtrate (1) Preparation and sterilization of birch sap medium The preparation procedures of birch sap medium were as described in Example 3.

(2) Preparation of unfermented birch sap filtrate

The birch sap medium was not subjected to inoculation and fermentation, and the preparation procedures of unfermented birch sap filtrate were as described in the step (4) of Example 3.

(3) The unfermented birch sap filtrate was determined for the content of total phenols and polysaccharides. The results were shown in Table 1.

Comparative Example 4: Preparation of Unfermented Birch Sap Filtrate (1) Preparation of birch sap medium The preparation and sterilization procedures of birch sap medium were as described in Example 4.

(2) Preparation of unfermented birch sap filtrate

The birch sap medium was not subjected to inoculation and fermentation, and the preparation procedures of unfermented birch sap filtrate were as described in the step (4) of Example 4.

(3) The unfermented birch sap filtrate was determined for the content of total phenols and polysaccharides. The results were shown in Table 1.

Comparative Example 5: Preparation of Yeast-Fermented Birch Sap Filtrate (1) Preparation of birch sap fermentation medium The preparation and sterilization procedures of birch sap fermentation medium were as described in Example 1.

(2) Preparation of yeast-fermented birch sap and filtrate thereof

According to the addition amount of 30 g/HL (hundred liters), 90 g of yeast freeze-dried powder was added to 1 L sterile normal saline and dispersed uniformly to obtain yeast seed broth; the yeast seed broth was inoculated into a 300 L fermentation tank, and continuously fermented at 30° C., 200 rmp, and an aeration of 1.2 vvm for 48 hours, then the fermentation operation was terminated to obtain a yeast-fermentation broth; and the yeast-fermented birch sap filtrate was obtained in the same manner as described in the step (4) of Example 1.

(3) The yeast-fermented birch sap filtrate was determined for the content of total phenols and polysaccharides. The results were shown in Table 1.

Comparative Example 6: Preparation of Yeast-Fermented Birch Sap Filtrate (1) Preparation of Birch Sap Fermentation Medium The preparation and sterilization procedures of birch sap fermentation medium were as described in Example 2.

(2) Preparation of yeast-fermented birch sap and filtrate thereof

According to the addition amount of 30 g/HL (hundred liters), 30 g of yeast freeze-dried powder was added to 350 mL sterile normal saline and dispersed uniformly to obtain yeast seed broth; the yeast seed broth was inoculated into a 100 L fermentation tank, and continuously fermented at 30° C., 180 rmp, and an aeration of 1.2 vvm for 48 hours, then the fermentation operation was terminated to obtain a yeast-fermentation broth; and the yeast-fermented birch sap filtrate was obtained in the same manner as described in the step (4) of Example 2.

(3) The yeast-fermented birch sap filtrate was determined for the content of total phenols and polysaccharides. The results were shown in Table 1.

Comparative Example 7: Preparation of Yeast-Fermented Birch Sap Filtrate (1) Preparation of birch sap fermentation medium The preparation and sterilization procedures of birch sap fermentation medium were as described in Example 3.

(2) Preparation of yeast-fermented birch sap and filtrate thereof

According to the addition amount of 30 g/HL (hundred liters), 150 g of yeast freeze-dried powder was added to 1.8 L sterile normal saline and dispersed uniformly to obtain yeast seed broth; the yeast seed broth was inoculated into a 500 L fermentation tank, and continuously fermented at 30° C., 200 rmp, and an aeration of 1.2 vvm for 48 hours, then the fermentation operation was terminated to obtain a yeast-fermentation broth; and the yeast-fermented birch sap filtrate was obtained in the same manner as described in the step (4) of Example 3.

(3) The yeast-fermented birch sap filtrate was determined for the content of total phenols and polysaccharides. The results were shown in Table 1.

Comparative Example 8: Preparation of Yeast-Fermented Birch Sap Filtrate (1) Preparation of birch sap fermentation medium The preparation and sterilization procedures of birch sap fermentation medium were as described in Example 4.

(2) Preparation of yeast-fermented birch sap and filtrate thereof

According to the addition amount of 30 g/HL (hundred liters), 90 g of yeast freeze-dried powder was added to 1 L sterile normal saline and dispersed uniformly to obtain yeast seed broth; the yeast seed broth was inoculated into a 300 L fermentation tank, and continuously fermented at 30° C., 180 rmp, and an aeration of 1.2 vvm for 48 hours, then the fermentation operation was terminated to obtain a yeast-fermentation broth; and the yeast-fermented birch sap filtrate was obtained in the same manner as described in the step (4) of Example 4.

(3) The yeast-fermented birch sap filtrate was determined for the content of total phenols and polysaccharides. The results were shown in Table 1.

TABLE 1

The content of total phenols and polysaccharides of the fermented birch sap filtrate obtained in Examples 1-5 and the birch sap filtrate obtained in Comparative Examples 1-8

| Items | Total phenols content (mg/L) | Polysaccharides content (g/L) |
|---|---|---|
| Example 1 | 185.0 | 4.4 |
| Example 2 | 168.0 | 5.2 |
| Example 3 | 153.5 | 4.7 |
| Example 4 | 137.1 | 3.0 |
| Example 5 | 131.0 | 1.8 |
| Comparative Example 1 | 25.3 | 0.06 |
| Comparative Example 2 | 22.5 | 0.05 |
| Comparative Example 3 | 19.4 | 0.03 |
| Comparative Example 4 | 18.2 | 0.03 |
| Comparative Example 5 | 28.5 | 0.1 |
| Comparative Example 6 | 25.0 | 0.7 |
| Comparative Example 7 | 22.4 | 0.06 |
| Comparative Example 8 | 20.7 | 0.06 |

The results showed that, the fermented birch sap filtrate produced by Inonotus obliquus contained extremely significantly higher contents of total phenols and polysaccharides than the unfermented birch sap filtrate and the birch sap filtrate fermented by conventional yeast, which greatly increased the activity of the product, thereby giving the possibility of using it in a skin topical composition.

Example 6: Test of Whitening Efficacy of Fermented Birch Sap Filtrate

In this example, the whitening efficacy of the fermented birch sap filtrate obtained in Examples 1-5 and the birch sap filtrate obtained in Comparative Examples 1-8 were evaluated based on tyrosinase activity inhibition rate, as follows.

(1) Evaluation principle of tyrosinase activity inhibition rate: tyrosinase (EC.1.14.18.1) is a key enzyme for melanin synthesis in organisms, catalyzes the hydroxylation of L-tyrosine to form L-dopa, and then oxidizes L-dopa to form dopaquinone, which is then subjected to a series of enzymatic and non-enzymatic reactions to form melanin. Therefore, the amount of melanin produced in organisms can be regulated by inhibiting the activity of tyrosinase.

(2) Reagents (a) PBS buffer (0.2M, pH 6.8): 51 mL of a 0.2M sodium dihydrogen phosphate solution and 49 mL of a 0.2M disodium hydrogen phosphate solution were mixed well.

(b) L-tyrosine (1.5 mM): 0.0272 g of L-tyrosine was predispersed with the PBS buffer, sonicated for 30 mins, transferred to a 100 mL volumetric flask, and constant-volumed with PBS buffer to scale;

(c) Tyrosinase (250U): tyrosinase (purchased from Sigma Aldrich) was dissolved in the PBS buffer, transferred to a 100 mL volumetric flask, constant-volumed with PBS buffer to scale to prepare a 250 U/mL of use solution.

(3) Experimental method: to four centrifuge tubes A, B, C, and D were added 0.25 mL L-tyrosine and 0.25 mL PBS, respectively. To the tubes B and D was additionally added 0.25 mL sample solution. To the tubes A and C was additionally added 0.25 mL PBS solution. The four tubes were vortex mixed well, held at a constant temperature of 37° C. for 10 mins, and to the tubes C and D was added 0.25 mL enzyme solution, and to the tubes A and B was added the same volume of PBS buffer to make up test sample volume. The four tubes were held at 37° C. for 20 mins. 200 microliters of the above test solutions were added to a 96-well plates, and the absorbance at 475 nm was detected with a microplate reader.

(4) Calculation of tyrosine activity inhibition rate

Tyrosinase activity inhibition rate %=((C−A)−(D−B))/(C−A)*100%

The results obtained were shown in Table 2 below.

TABLE 2

Comparison of tyrosinase activity inhibition rates of the fermented birch sap filtrate obtained in Examples 1-5 and the birch sap filtrate obtained in Comparative Examples 1-8

| Items | Tyrosinase activity inhibition rate |
|---|---|
| Example 1 | 96.8% |
| Example 2 | 95.7% |
| Example 3 | 96.0% |
| Example 4 | 91.85% |
| Example 5 | 71.0% |
| Comparative Example 1 | 2.3% |
| Comparative Example 2 | 5.9% |
| Comparative Example 3 | 3.5% |
| Comparative Example 4 | 3.7% |
| Comparative Example 5 | 8.8% |
| Comparative Example 6 | 1.5% |
| Comparative Example 7 | 5.2% |
| Comparative Example 8 | −1.9% |

The results showed that, the fermented birch sap filtrate produced by Inonotus obliquus exhibited extremely significantly higher tyrosinase activity inhibition rates than the unfermented birch sap filtrate and the birch sap filtrate fermented by conventional yeast, which showed that the fermented birch sap filtrate produced by Inonotus obliquus had significant whitening efficacy, and thus can be used in skin topical composition having whitening efficacy, especially in whitening cosmetic composition.

Example 7: Test of Antioxidation of Fermented Birch Sap Filtrate

In this example, the antioxidations of the fermented birch sap filtrate obtained in Examples 1-5 and the birch sap filtrate obtained in Comparative Examples 1-8 were evaluated based on hydroxyl radical scavenging rate and DPPH radical scavenging rate, as follows.

1. Hydroxyl radical scavenging rate
   (1) Test principle: it is known that the mixture of $FeCl_3$-EDTA, hydrogen peroxide and ascorbic acid will react at pH 7.4 to produce hydroxyl radicals, the hydroxyl radicals can degrade deoxyribose to form malondialdehyde; at low pH, the product malondialdehyde (MDA) and thiobarbituric acid (TBA) are heated to produce pink chromophores, and the hydroxyl radical content can be determined based on the content of the pink chromophores.
   (2) Test method: three groups of reaction reagents were prepared, including (A) 75 μL 0.8 mM $FeCl_3$+75 μL 4 mM EDTA+600 μL 4 mM $KH_2PO_4$—KOH buffer+2.0565 mL distilled water+43.5 μL 3% $H_2O_2$+75 μL 112 mM deoxyribose+75 μL 4 mM ascorbic acid; (B)75 μL 0.8 mM $FeCl_3$+75 μL 4 mM EDTA+600 μL 4 mM $KH_2PO_4$-KOH buffer+2.0565 mL sample solution+43.5 μL 3% $H_2O_2$+75 μL 112 mM deoxyribose+75 μL 4 mM ascorbic acid; (C)75 μL 0.8 mM $FeCl_3$+75 μL 4 mM EDTA+600 μL 4 mM $KH_2PO_4$-KOH buffer+2.0565 mL sample solution+43.5 μL 3% $H_2O_2$+75 μL 4 mM ascorbic acid. The reaction mixtures of all groups were incubated in a constant temperature water bath at 37° C. for 1 h, and then, to the mixtures was added 2 mL of 0.6% TBA, heated in a boiling water bath for 15 mins, cooled rapidly, and centrifuged. The supernatant was determined for absorbance at 450 nm, 532 nm, and 600 nm.
   (3) Calculation method Hydroxyl radical scavenging rate (%)=[1−(B−C)/A]*100%

2. DPPH radical scavenging rate
   (1) Test principle: DPPH radical is a single-electron radical, which has a characteristic absorption at 517 nm. Free radical scavenger can be paired with the single-electron of DPPH radical to make its absorption at 517 nm disappear, and the degree of discoloration has a quantitative relationship with the number of electrons it accepts, from which the scavenging ability of the free radical scavenger is inferred.
   (2) Test method: three groups of reaction reagents were prepared and mixed, including (A) 1 mL distilled water+3 mL 0.1 mM DPPH reaction solution; (B) 1 mL sample solution+3 mL 0.1 mM DPPH reaction solution; (C) 1 mL sample solution+3 mL ethanol. All groups were shaken well and reacted in dark at room temperature for 30 mins, and then determined for absorbance at 517 nm.
   (3) Calculation method DPPH radical scavenging rate (%)=[1−(B−C)/A]*100%

The results obtained are shown in Table 3 below.

TABLE 3

Hydroxyl radical scavenging rates and DPPH radical scavenging rates of the fermented birch sap filtrate obtained in Examples 1-5 and the birch sap filtrate obtained in Comparative Examples 1-8

| Items | Hydroxyl radical scavenging rate | DPPH radical scavenging rate |
|---|---|---|
| Example 1 | 54.7% | 72.5% |
| Example 2 | 48.8% | 70.8% |
| Example 3 | 52.1%% | 71.5% |
| Example 4 | 50.5% | 69.0% |
| Example 5 | 40.7% | 45.1% |
| Comparative Example 1 | 7.0% | 11.2% |
| Comparative Example 2 | 5.4% | 10.4% |
| Comparative Example 3 | 5.3% | 8.3% |
| Comparative Example 4 | 6.1% | 8.4% |
| Comparative Example 5 | 6.4% | 12.0% |
| Comparative Example 6 | 5.5% | 9.7% |
| Comparative Example 7 | 5.7% | 8.7% |
| Comparative Example 8 | 3.3% | 9.0% |

The results showed that, the fermented birch sap filtrate produced by Inonotus obliquus exhibited extremely significantly higher hydroxyl radical scavenging rates and DPPH radical scavenging rates than the unfermented birch sap filtrate and the birch sap filtrate fermented by conventional yeast, which showed that the fermented birch sap filtrate produced by Inonotus obliquus had significant antioxidation effect, and thus can be used in skin topical composition having antioxidation effect, especially in antioxidant cosmetic composition.

Example 8: Preparation of Whitening Toner

In this example, the fermented birch sap filtrate prepared in Example 1 was used to prepare a whitening toner, and the formulation was as follows:

| Ingredients | Content (mass %) |
| --- | --- |
| Fermented birch sap filtrate | 95.65 |
| Sodium benzoate | 0.35 |
| 1,2-pentanediol | 4 |

The toner was prepared as follows: the fermented birch sap filtrate, sodium benzoate and pentanediol were mixed and filtered.

Example 9: Preparation of Antioxidant Face Cream

In this example, the fermented birch sap filtrate prepared in Example 3 was used to prepare a face cream, and the formulation was as follows:

| Ingredients | Content (mass %) |
| --- | --- |
| Fermented birch sap filtrate | 83.45 |
| Caprylic/capric triglyceride | 3 |
| Shea Butter | 5 |
| C16 alcohol | 2 |
| Polyethylene glycol ether mixture | 3 |
| Methyl isothiazolinone | 0.1 |
| Amino acid moisturizer | 3.0 |
| Sodium benzoate | 0.3 |
| fragrance | 0.15 |

The face cream was prepared as follows: the oil phase ingredients and the aqueous phase ingredients in the above formulation were mixed, respectively, and heated to 75° C. to prepare an oil phase and an aqueous phase, respectively; the resulting oil phase and aqueous phase were homogenized and emulsified in a vacuum homogenizer, cooled to 45° C., added with fragrance and sodium benzoate, and mixed well.

The technical solutions of the above-mentioned examples are preferred embodiments of the present invention. Various modifications and variations can be made without departing from the principle of the present invention, and these modifications and variations should also be considered within the scope of the present invention.

The invention claimed is:

1. A fermented birch sap which is obtained by:
 (i) fermentation of a medium comprising a substrate and a strain,
 (ii) in situ thermal extracting of the medium, and
 (iii) centrifugation of the medium performed at 6,000-10,000 rpm for 15-30 minutes to remove mycelia,
 wherein the substrate comprises birch sap in an amount of 90% or more by weight of the medium, and the strain comprises Inonotus obliquus; and
 wherein the fermented birch sap comprises birch sap, total phenols of 100 mg/L or more, and polysaccharides of 1.3 g/L or more, and
 wherein the phenols comprise one or more of ferulic acid, naringin, quercetin, and kaempferol.

2. The fermented birch sap according to claim 1, comprising total phenols of 130 mg/L or more and polysaccharides of 1.8 g/L or more.

3. The fermented birch sap according to claim 1, comprising total phenols of 150 mg/L or more and polysaccharides of 3.0 g/L or more.

4. A skin topical composition comprising a fermented birch sap according to claim 1.

5. The fermented birch sap according to claim 1, wherein the birch sap is obtained from Betula Betulaceae, Betula pubescens, Betula Pendula, or Betula platyphylla.

6. The fermented birch sap according to claim 1, wherein the phenols further comprise gallic acid.

7. The fermented birch sap according to claim 1, wherein the fermentation occurs at a temperature of about 25-30° C., a stirring speed of 180-250 rpm, and an aeration rate of 1.2-2.0 vvm for 7-9 days.

8. The fermented birch sap according to claim 1, wherein the strain is incubated at a temperature of 25-30° C. and a shaker speed of 150-180 rpm for 4-6 days prior to combination with the substrate in the medium.

\* \* \* \* \*